US009360455B2

(12) United States Patent
Campbell et al.

(10) Patent No.: US 9,360,455 B2
(45) Date of Patent: Jun. 7, 2016

(54) METHODS FOR ANALYSIS OF ISOMERIC LIPIDS

(71) Applicant: DH TECHNOLOGIES DEVELOPMENT PTE. LTD., Singapore (SG)

(72) Inventors: John L. Campbell, Milton (CA); Yves Leblanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/655,263

(22) PCT Filed: Dec. 13, 2013

(86) PCT No.: PCT/IB2013/002755
§ 371 (c)(1),
(2) Date: Jun. 24, 2015

(87) PCT Pub. No.: WO2014/102577
PCT Pub. Date: Jul. 3, 2014

(65) Prior Publication Data
US 2015/0316507 A1    Nov. 5, 2015

Related U.S. Application Data

(60) Provisional application No. 61/745,923, filed on Dec. 26, 2012, provisional application No. 61/876,611, filed on Sep. 11, 2013.

(51) Int. Cl.
G01N 33/92    (2006.01)
G01N 27/62    (2006.01)
H01J 49/00    (2006.01)
H01J 49/04    (2006.01)

(52) U.S. Cl.
CPC ............ G01N 27/624 (2013.01); G01N 27/622 (2013.01); G01N 33/92 (2013.01);
(Continued)

(58) Field of Classification Search
CPC ..... G01N 33/20; G01N 33/92; G01N 27/622;
G01N 27/624; G01N 2458/15; H01J 49/00;
H01J 49/0027; H01J 49/004; Y10T 436/16;
Y10T 436/17; Y10T 436/173845; Y10T
436/18; Y10T 436/20; Y10T 436/200833;
Y10T 436/203332; Y10T 436/24
USPC ......... 436/71, 73, 79, 80, 103, 106, 111, 119,
436/127, 128, 131, 173; 250/281, 282, 283;
356/326
See application file for complete search history.

(56) References Cited

U.S. PATENT DOCUMENTS

2009/0294650 A1 * 12/2009 Schneider ............. H01L 49/004
250/282
2015/0260684 A1 * 9/2015 Blanksby ............. G01N 27/622
250/288

OTHER PUBLICATIONS

Shvartsburg et al. Journal of the American Society for Mass Spectrometry, vol. 22, Apr. 12, 2011, pp. 1146-1155.*

(Continued)

*Primary Examiner* — Maureen Wallenhorst (57) ABSTRACT

A method for analyzing a sample that contains a plurality of lipid isomers is described that involves forming one or more lipid metal ion adducts and transporting the one or more lipid metal ion adducts through a differential mobility spectrometer to cause separation of the one or more lipid metal ion adducts from each other. The lipid isomers can be chosen, for example, from fatty acids, glycerolipids, glycerophospholipids, sphingolipids, saccharolipids, polyketides, sterol lipids, and prenol lipids. Particular examples include phosphatidylcholine regioisomers such as 1-palmatoyl-2-oleoyl-sn-phosphatidylcholine (POPC) and 1-oleoyl-2-palmatoyl-sn-phosphatidylcholine and triacylglycerols containing palmetic and oleic acid groups. The metal chosen can include a cationization reagent that contains sodium, potassium, silver or lithium.

13 Claims, 7 Drawing Sheets

(52) U.S. Cl.
CPC ......... *H01J49/0031* (2013.01); *H01J 49/0422* (2013.01); *G01N 2458/15* (2013.01); *Y10T 436/24* (2015.01)

(56) References Cited

OTHER PUBLICATIONS

Jackson et al. Journal of the American Society for Mass Spectrometry, vol. 19, Jul. 16, 2008, pp. 1655-1662.*

Blagojevic et al. Analytical Chemistry, vol. 83, Apr. 5, 2011, pp. 3470-3476.*

Clowers et al. Journal of Mass Spectrometry, vol. 41, Jan. 23, 2006, pp. 339-351.*

Trimpin et al. International Journal of Mass Spectrometry, vol. 287, Jan. 8, 2009, pp. 58-69.*

* cited by examiner

METHODS FOR ANALYSIS OF ISOMERIC LIPIDS

CROSS REFERENCE TO RELATED APPLICATIONS

This application is a national stage filing under 35 U.S.C. 371 of PCT/IB2013/002755 filed on Dec. 13, 2013, which designates the U.S., and which claims the benefit of U.S. Provisional Patent Application Nos. 61/745,923, filed Dec. 26, 2012, and 61/876,611, filed Sep. 11, 2013, the contents of which are incorporated by reference herein in their entireties.

FIELD

The invention generally relates to mass spectrometry, and more particularly to methods and apparatus for the separation and/or quantitation of isomeric lipids using ion mobility spectrometry.

INTRODUCTION

*H01J 49/00*
(2006.01)
*H01J 49/04*
(2006.01)

Despite the structural similarity of isomeric species, their biological activity can vary drastically. Moreover, the presence of a particular isomer and/or the relative abundance of the isomers can be used in medical diagnostics. Traditional mass spectrometry (MS) techniques, however, are sometimes inadequate to discriminate between two or more isomeric species in a sample.

For example, regioisomers are molecules that contain the same core structure and side chains, though the side chains can be arranged in more than one position. Despite the recognition that certain regioisomers can serve as critical biomarkers for disease and/or provide information regarding the underlying biomolecular machinery based, for example, on the relative abundance of the various regioisomers in tissues (i.e., brain vs. kidneys), prior biochemical or MS-based techniques have been inadequate to resolve the isomeric species for quantitation in a biological sample, e.g., by resolving their respective mass spectra.

By way of example, the differentiation of phosphatidylcholine (PC) regioisomers has challenged lipid biochemists for many years The two most common regioisomers for PC are 1-palmatoyl-2-oleoyl-sn-phosphatidylcholine (POPC) and 1-oleoyl-2-palmatoyl-sn-phosphatidylcholine, as shown below:

1-Palmatoyl-2-oleoyl-sn-phosphatidtylcholine (POPC)

-continued

1-Oleoyl-2-palmatoyl-sn-phosphatidtylcholine (OPPC)

Though both positive-mode and negative-modes of MS/MS have shown some promise in individually quantifying POPC and OPPC based on the diagnostic fragment ions present in their MS/MS fragmentation spectra, it nonetheless remains difficult to quantify a particular species in a mixture containing both isomers as their fragmentation behavior is essentially identical. Further, no chromatographic separation is presently available. Indeed, when OPPC and POPC are both present, their MS/MS fragmentation spectra are convolved such that these lipid regioisomers are generally analyzed and quantified in tandem (e.g., without enumerating the abundance of each particular isomer).

Similarly, many other isomeric lipids, including but not limited to triacylglycerols (TAGs) and diacylglycerols (DGs), are difficult to quantify individually when present in a mixture.

Glycerolipids, including triacylglycerols (TAGs), are very important compounds in many different arenas, including biofuels, food processing, and nutritional supplements. These molecules are also especially challenging analytes to characterize as each individual TAG, which contains three acyl chains, can be present as a mixture of structural isomers. For example, a TAG containing two palmetic acid group (P) and one oleic acid group (O) could have one of three isomer forms: PPO, POP, or OPP. All three forms have the same molecular weight and, as such, would have the same m/z value when analyzed by a mass spectrometer.

While liquid chromatography has been used to separate glycerolipid (TAG) isomers, such experiments generally require very specialized columns (e.g., chiral stationary phases) and long gradient times (>2 hours).

Accordingly, there remains a need for improved quantitation of isomeric lipids with enhanced discrimination between species.

SUMMARY

It has been unexpectedly discovered that the reaction of a cationization agent with lipid isomers, including but not limited to lipid regioisomers such as POPC and OPPC or PPO, POP and OPP can advantageously allow separation of the ionized lipids using differential mobility spectrometry. The resolution of the ion signals can in turn allow accurate quantification of such isomeric lipids in a sample containing them.

In accordance with one aspect, certain embodiments of the applicant's teachings relate to a method for analyzing a sample. According to the method, a sample containing or suspected of containing a plurality of lipid isomers is ionized so as to form one or more lipid ions. The method also includes transporting the one or more lipid ions through a differential mobility spectrometer to effect separation of their separation. In accordance with various aspects of applicants present teachings, certain embodiments relate to a method for analyzing a sample that includes ionizing a sample containing or suspected of containing a plurality of lipid isomers so as to form one or more lipid metal ion adducts and transporting the one or more lipid metal ion adducts through a differential mobility spectrometer to effect separation of the one or more lipid metal ion adducts.

In some aspects, ionizing the sample can comprise reacting the sample with a cationization reagent. For example, the cationization reagent comprises a salt of any of sodium, potassium, silver, and lithium.

In various aspects, the lipid isomers can be selected from the group comprising fatty acids, glycerolipids, glycerophospholipids, sphingolipids, saccharolipids, polyketides, sterol lipids, and prenol lipids. In some aspects, an acyl chain of the lipid isomers can comprise at least one unsaturated carbon. In some aspects, the unsaturated carbon includes a carbon-carbon double bond.

In one aspect, the plurality of lipid isomers can comprise OPPC and POPC. In a related aspect, ionizing the sample can comprise reacting the sample with one of silver and lithium.

In one aspect, the plurality of lipid isomers can comprise POP, PPO or OPP.

In various aspects, the method can include determining the relative abundance of the plurality of lipid isomers in the sample.

In some aspects, the method can further include increasing a throttle gas flow rate to increase a drift time of the lipid metal ion adducts in the differential mobility spectrometer.

In some aspects, the sample is not passed through a liquid chromatography column prior to being transmitted through the differential mobility spectrometer. The differential mobility spectrometer can have a variety of configurations. For example, the differential mobility spectrometer can comprise FAIMS.

In accordance with various aspects of applicants present teachings, certain embodiments relate to a method of mass spectrometry, comprising exposing a sample comprising a plurality of isomeric lipids to a cationization reagent so as to stabilize a configuration of said plurality of isomeric lipids. The method can further comprise transporting said stabilized isomeric lipids through an ion mobility spectrometer so as to effect separation of said plurality of one or more stabilized isomeric lipids.

In accordance with various aspects of applicants present teachings, certain embodiments relate to a method for analyzing a sample containing or suspected of containing a plurality of isomeric lipids. The method can comprise, for example, forming metal ion adducts with said isomeric lipids and transporting said one or more lipid metal ion adducts through a differential mobility spectrometer to effect separation of said one or more lipid metal ion adducts.

In accordance with various aspects of applicants teachings, certain embodiments relate to a method for analyzing a sample. The method can comprise: ionizing a sample containing or suspected of containing a plurality of lipid isomers so as to form one or more lipid metal ion adducts; transporting said one or more lipid metal ion adducts through a differential mobility spectrometer to effect separation of said one or more lipid metal ion adducts; and enhancing the separation of the lipid metal ion adducts by the addition of a chemical modifier to the differential mobility spectrometer.

In some aspects, ionizing the sample can comprise reacting the sample with a cationization reagent. For example, in addition to the above, the cationization reagent can comprise a salt of any of an alkali metal, alkali earth metal, or a transition metal.

In some aspects, the chemical modifier used in the differential mobility cell is selected from the group of alcohols, aldehydes, amides, amines, aromatics, esters, ethers, halocarbons, ketones, nitriles, thiols, or water. In some aspects, the chemical modifier is propanol.

In some aspects, the plurality of lipid isomers comprises isomeric triacylglycerol molecules. In various aspects, the triacylglycerol molecules comprise two palmetic acid groups and one oleic acid group.

In some aspects, the chemical modifier is propanol and the cationization reagent is a salt of silver.

In some aspects, the method(s) described above can further include determining the relative abundance of the plurality of lipid isomers in the sample.

In some aspects, the method(s) described above can further include increasing a throttle gas flow rate to increase a residence time for the lipid metal ion adducts in the differential mobility spectrometer.

In some aspect, the method(s) described above can further include adding chemical modifier to the differential mobility spectrometer to enhance the separation of the plurality of lipid isomers in the sample.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

Methods and systems for separating and/or quantifying isomeric lipids using ion mobility spectrometry are provided herein. In accordance with various aspects of the applicants' teachings, the methods and systems can provide for the separation of isomeric lipids, for example, those isomeric lipid that may be difficult to separate with conventional MS techniques. In various aspects, methods and systems in accordance with applicant's teachings can enable a differential mobility spectrometer to resolve a sample's isomeric lipids such as POPC and OPPC, and various isomeric TAGs such as POP, PPO and OPP and DGs, all by way of non-limiting example.

Figure 1:
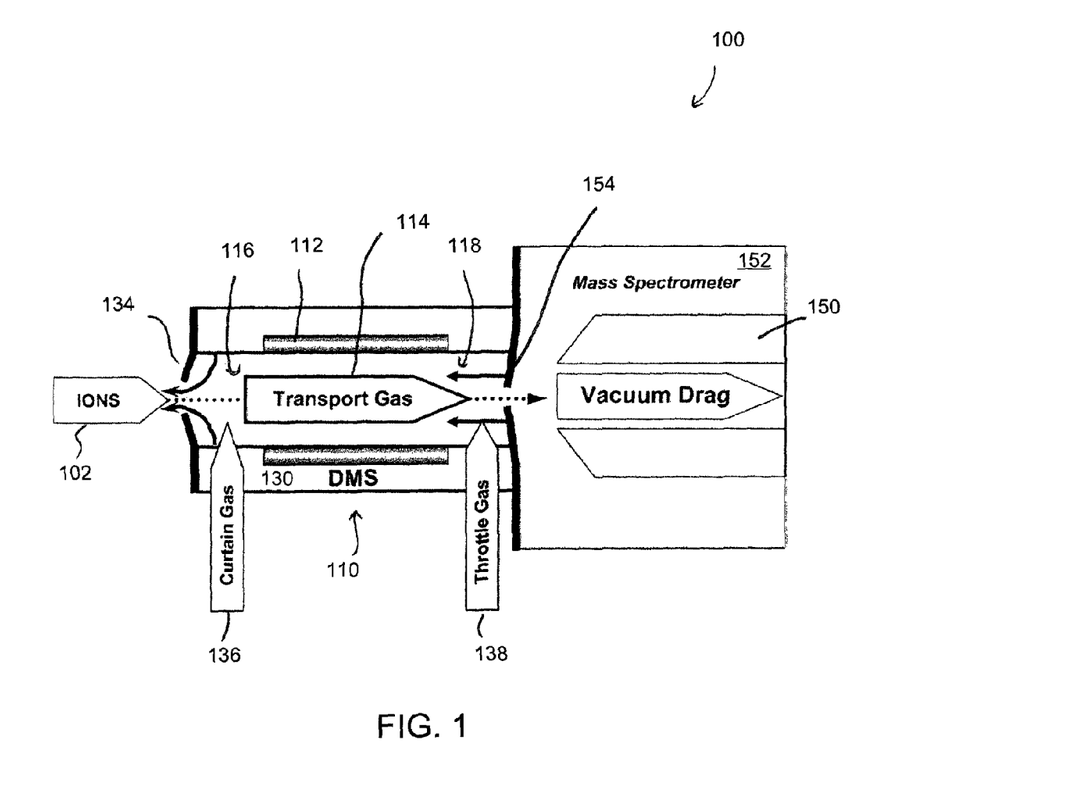
FIG. 1, in a schematic diagram, illustrates an exemplary differential mobility spectrometer/mass spectrometer system including a curtain gas supply and a throttle gas supply in accordance with an aspect of various embodiments of the applicant's teachings.

With reference now to FIG. 1, an exemplary differential mobility spectrometer/mass spectrometer system 100 in accordance with various aspects of applicant's teachings is illustrated schematically. As shown in FIG. 1, the differential mobility spectrometer/mass spectrometer system 100 generally comprises a differential mobility spectrometer 110 in fluid communication with a first vacuum lens element 150 of a mass spectrometer (hereinafter generally designated mass spectrometer 150). As will be appreciated by a person skilled in the art, the differential mobility spectrometer/mass spectrometer system 100 represents only one possible configuration for use in accordance with various aspects of the systems, devices, and methods described herein.

The differential mobility spectrometer 110 can have a variety of configurations, but is generally configured to resolve ions based on their mobility through a fixed or variable electric field (whereas MS analyzes ions based on their mass-to-charge ratios, which is identical in parent isomeric molecules, and often nearly identical in their fragment ions). For example, the mobility spectrometer can be an ion mobility spectrometer, a differential mobility spectrometer, a drift-time ion mobility spectrometer, traveling wave ion mobility spectrometry (TWIMS) device, trapped ion mobility spectrometry, or high-field asymmetric waveform ion mobility spectrometry (FAIMS) devices of various geometries such as parallel plate, curved electrode, or cylindrical FAIMS device, among others. In DMS, RF voltages, often referred to as separation voltages (SV), can be applied across the drift tube in a direction perpendicular to that of a drift gas flow. Ions of a given species tend to migrate radially away from the axis of the transport chamber by a characteristic amount during each cycle of the RF waveform due to differences in mobility during the high field and low field portions. A DC potential, commonly referred to as a compensation voltage (CV or CoV), applied to the drift tube provides a counterbalancing electrostatic force to that of the SV. The CV can be tuned so as to preferentially prevent the drift of a species of ion of interest. Depending on the application, the CV can be set to a fixed value to pass only ion species with a particular differential mobility while the remaining species of ions drift toward the electrodes and are neutralized. Alternatively, if the CV is scanned for a fixed SV as a sample is introduced continuously into the DMS, a mobility spectrum can be produced as the DMS transmits ions of different differential mobilities.

In the exemplary embodiment depicted in FIG. 1, the differential mobility spectrometer 110 is contained within a curtain chamber 130 that is defined by a curtain plate or boundary member 134 and is supplied with a curtain gas 136 from a curtain gas supply (not shown). As shown, the exemplary differential mobility spectrometer 110 comprises a pair of opposed electrode plates 112 that surround a transport gas 114 that drifts from an inlet 116 of the differential mobility spectrometer 110 to an outlet 118 of the differential mobility spectrometer 110. The outlet 118 of the differential mobility spectrometer 110 releases the drift gas 116 into an inlet 154 of a vacuum chamber 152 containing the mass spectrometer 150. A throttle gas 138 can additionally be supplied at the outlet 118 of the differential mobility spectrometer 110 so as to modify the flow rate of transport gas 114 through the differential mobility spectrometer 110.

In accordance with certain aspect of the present teachings, the curtain gas 136 and throttle gas 114 can be set to flow rates determined by a flow controller and valves so as to alter the drift time of ions within the differential mobility spectrometer 110. Each of the curtain and throttle gas supplies can provide the same or different pure or mixed composition gas to the curtain gas chamber. By way of non-limiting example, the curtain gas can be air, $O_2$, He, $N_2$, $CO_2$, or any combination thereof. Additionally, the system 110 can also include a modifier supply (not shown) for supplying a modifier and/or reagent to the curtain and throttle gases. The modifier can be selected from the group of alcohols, aldehydes, amides, amines, aromatics, esters, ethers, halocarbons, ketones, nitriles, thiols, and water, preferably the chemical modifier is propanol. The pressure of the curtain chamber 130 can be maintained, for example, at or near atmospheric pressure (i.e., 760 Torr).

Ions 102 can be provided from an ion source (not shown) and emitted into the curtain chamber 130 via curtain chamber inlet 150. As will be appreciated by a person skilled in the art, the ion source can be virtually any ion source known in the art, including for example, an electrospray ionization (ESI) source. The pressure of the curtain gases in the curtain chamber 130 (e.g., ~760 Torr) can provide both a curtain gas outflow out of curtain gas chamber inlet, as well as a curtain gas inflow into the differential mobility spectrometer 110, which inflow becomes the transport gas 114 that carries the ions 102 through the differential mobility spectrometer 110 and into the mass spectrometer 150 contained within the vacuum chamber 152, which can be maintained at a much lower pressure than the curtain chamber 130. By way of non-limiting example, the vacuum chamber 152 can be maintained at a pressure lower than that of the curtain chamber 130 (e.g., by a vacuum pump) so as to drag the transport gas 114 and ions 102 entrained therein into the inlet 154 of the mass spectrometer 150.

As will be appreciated by a person skilled in the art, the differential mobility/mass spectrometer system 100 can additionally include one or more additional mass analyzer elements downstream from vacuum chamber 152. Ions can be transported through vacuum chamber 152 and through one or more additional differentially pumped vacuum stages containing one or more mass analyzer elements. For instance, in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage can contain a detector, as well as two quadrupole mass analyzers with a collision cell located between them. It will be apparent to those skilled in the art that there may be a number of other ion optical elements in the system. Alternatively, a detector (e.g., a Faraday cup or other ion current measuring device) effective to detect the ions transmitted by the differential mobility spectrometer 110 can be disposed directly at the outlet of the differential mobility spectrometer 110.

In accordance with various aspects of the applicant's teachings, the exemplary system discussed above with reference to FIG. 1 can be used to analyze one or more ionized isomeric lipids contained within a sample. In accordance with certain aspects of the present teachings, a lipid molecule (M) contained within a sample can be ionized, for example, by reacting the lipid molecule with a cationization agent ($X^+$) so as to form a cationized lipid molecule ($[M+X]^+$). By way of example, the lipid molecule can be protonated so as to form a protonated lipid molecule ($[M+H]^+$). Cationized lipid molecules can alternatively be formed by associating the lipid molecules with a metal ion such as sodium, potassium, silver, or lithium so as to generate a cationized lipid-metal ion adduct such as [M+Na]$^+$, [M+K]$^+$, [M+Ag]$^+$, and [M+Li]$^+$, respectively, all by way of non-limiting example.

In accordance with various aspects of the present teachings, for example, applicants have discovered that by associating isomeric lipids with a cationization agent so as to form one or more cationized lipid molecules (including by protonation), differential mobility spectrometry can enable improved separation of the cationized isomeric species. By way of example, isomer-metal ion adducts, formed via exposure to a mixture of isomeric lipids to metal cations, can be sufficiently separated using differential mobility spectrometry so as to allow the independent quantitation of the lipids from which the isomer-metal ion adducts were derived. Without being bound to any particular theory, it is believed that the association of the lipids with the metal cations can help lock the lipids into stable configurations that exhibit a resolvable, characteristic response when subjected to differential mobility spectrometry.

Accordingly, in operation, a sample containing or suspected of containing two or more isomeric lipids can be adducted with a metal ion, for example, so as to form lipid-metal ion adducts corresponding to each of the two or more isomeric species. As discussed above, the sample containing lipid-metal ion adducts can be emitted into the curtain chamber 130 (e.g., from an ion source such as ESI) and transported through the differential mobility spectrometer 110 to effect separation of various lipid-metal ion adducts. According to various aspects, the differential mobility spectrometer 110 can be operated at a fixed SV with the CV scanned so as to serially pass various ions. The ions transmitted by the differential mobility spectrometer can then be sent to downstream mass analyzer elements 150 for detection and/or further analysis.

EXAMPLES

The applicants' teachings can be even more fully understood with reference to the following examples and data presented in FIGS. 2-7, which demonstrate the separation of various isomeric lipids present in a sample using differential mobility spectrometry in accordance with various aspects of the teachings herein. Other embodiments of the applicants' teachings will be apparent to those skilled in the art from consideration of the present specification and practice of the present teachings disclosed herein. It is intended that these examples be considered as exemplary only.

Figure 2:
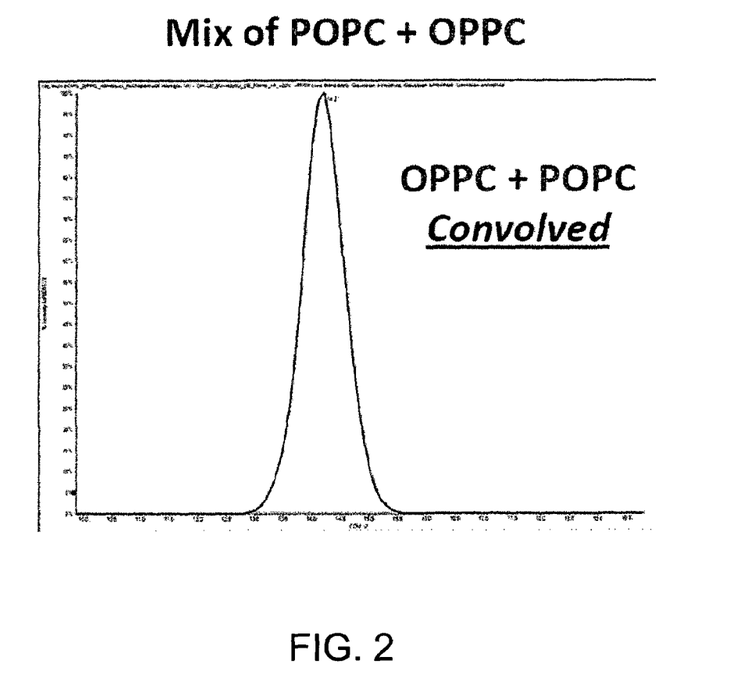
FIG. 2 depicts data for a mixture containing POPC and OPPC as transmitted by a differential mobility spectrometer and subsequently detected in accordance with prior art techniques.

As noted above, POPC and OPPC are lipid regioisomers that can be present in biological tissue, though their relative abundance often differs depending on the tissue type. Despite the improved understanding of physiological processes that could result from determining their relative abundance, prior work using mass spectrometric techniques often fail to resolve these isomeric lipids in a manner that would allow for their reliable quantitation. For example, with reference now to FIG. 2, when a sample containing a mixture of POPC and OPPC is ionized and transmitted through a differential mobility spectrometer in accordance with prior techniques, the exemplary data indicates that the individual isomers cannot be resolved. Rather, as shown in FIG. 2, the peaks are convolved such that one could not determine the relative abundance of POPC and OPPC.

However, with reference now to FIGS. 3-6, the exemplary data depicts that DMS can be utilized to separate POPC-metal ion adducts from OPPC-metal ion adducts in accordance with various aspects of the applicants' present teachings.

Two regioisomeric phosphatidylcholines, 16:0-18:1 (POPC) and 18:1-16:0 (OPPC), as well as bovine heart total extract, were obtained from Avanti Polar Lipids, Inc. and used without further purification. Lithium carbonate and silver acetate, as well as egg yolk PC extract were obtained from Sigma-Aldrich (St. Louis, Mo.) and used without further purification. HPLC-grade methanol (J.T. Baker, Avantor Performance Chemicals, Center Valley, Pa.) was also used without further purification. Distilled deionized water (15 MΩ) was produced in-house using a Millipore (Billerica, Mass.) Integral 10 water purification system.

Cow (*Bos taurus* L.) brain and kidneys were also collected from the Wollondilly Abattoir (Picton, NSW, Australia) immediately following the death of the animals. Organs were transported on ice, then stored at −80° C., with lipid extraction performed as previously described (Nealon et al., 2008). Cow brain and kidney extracts were diluted to a final concentration of ~50 μM with the addition of methanol containing either lithium carbonate or silver acetate (present at ~50 μM) before being infused into the mass spectrometer.

Differential Mobility Spectrometry-Mass Spectrometry.

A differential mobility spectrometer (SelexION™, AB SCIEX, Concord, ON) system (Campbell et al., 2012) was mounted on a 5500 QTRAP® system (AB SCIEX), between a TurboV™ ESI source and the mass spectrometer's sampling orifice. The ESI probe was maintained at a voltage of 4800 V, with a source temperature of 150° C., nebulizing gas pressure of 30 psi, and auxiliary gas pressure of 20 psi. The DMS temperature was maintained at 150° C., and nitrogen was used as the curtain gas (20 psi), throttle gas (variable), and target gas (~3 mTorr) for the MS/MS experiments. In each experiment, an analyte solution (10 ng/mL) was infused into the ESI source at a rate of 20 μL/min.

For the DMS experiments conducted in this study, the separation voltage (SV) was held at an optimum value (+4000 V, 133 Td) while the compensation voltage (CV) was scanned from −15V to +15V in 0.1-V increments.

At each incremental value of CV, an MS/MS spectrum of the ionized PC lipid was recorded. These data were plotted as ionograms, with signal intensity on the y-axis and CV on the x-axis.

Tandem mass spectrometry (MS/MS) experiments were conducted using the enhanced product ion (EPI) scan mode (Hager and Le Blanc, 2003) of the QTRAP® mass spectrometer. Each MS/MS experiment was conducted under identical instrumental conditions: identical precursor ions, 10-ms fill time, collision energy of 55 eV$_{Lab}$, ~3 mTorr of N$_2$ target gas. Fragment and residual precursor ions were mass analyzed over the range of m/z 100-800 by mass-selective axial ejection (MSAE) (Londry and Hager, 2003).

The following table depicts the relative abundance of POPC and OPPC in the above-referenced tested samples:

|  | OPPC | POPC | % OPPC | % POPC |
| --- | --- | --- | --- | --- |
| Kidney | 1.31E+06 | 2.04E+07 | 6.0% | 94.0% |
| Brain | 1.46E+07 | 9.88E+07 | 12.9% | 87.1% |
| Egg Yolk | 2.24E+07 | 1.30E+09 | 1.7% | 98.3% |
| BHE | 0.00E+00 | 0.00E+00 | N/A | N/A |
| POPC (Avanti) | 2.51E+06 | 1.08E+07 | 18.9% | 81.1% |
| OPPC (Avanti) | 6.80E+07 | 3.93E+05 | 99.4% | 0.6% |

Figure 3:
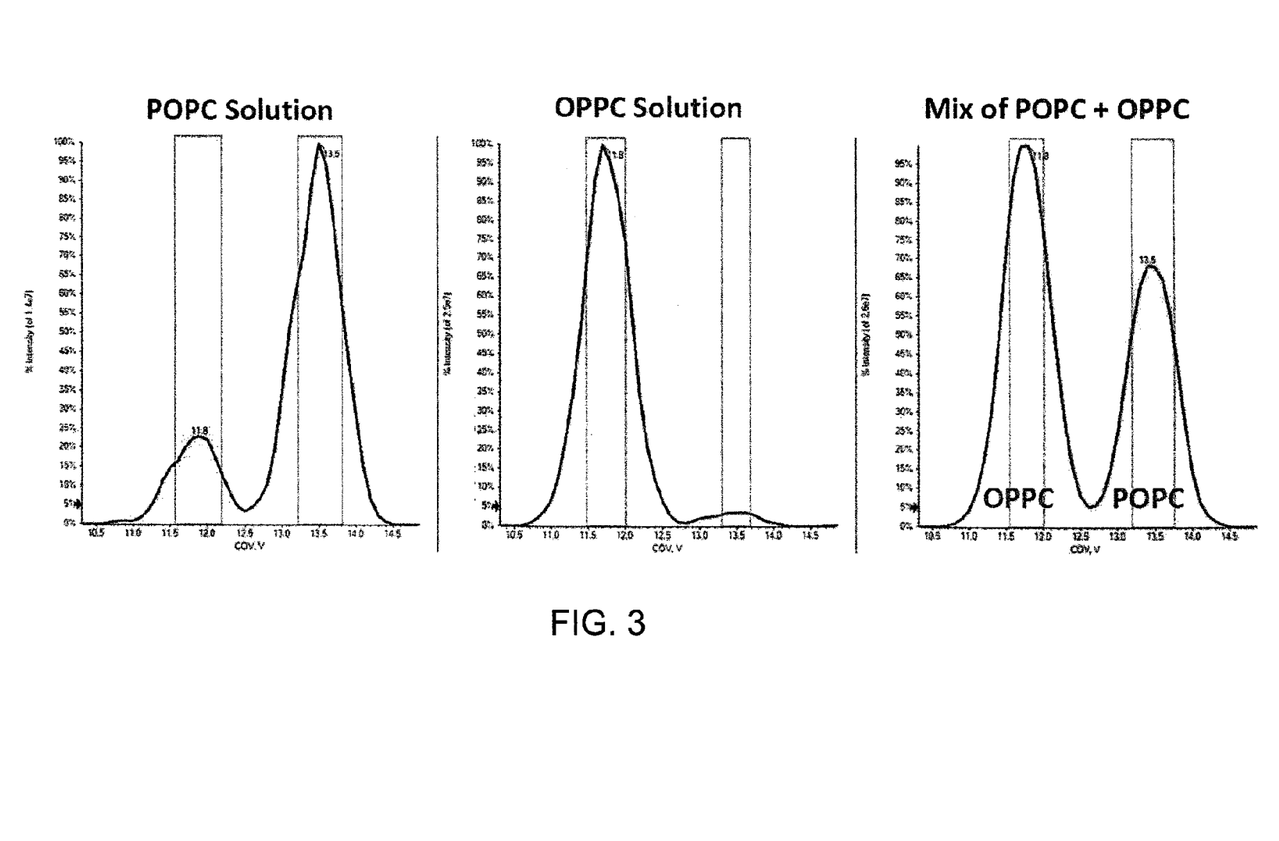
FIG. 3 depicts data for [POPC+Ag]$^+$ adduct, [OPPC+Ag]$^+$, and a mixture thereof as transmitted by a differential mobility spectrometer and subsequently detected in accordance with aspects of various embodiments of the applicant's teachings.
Figure 4:
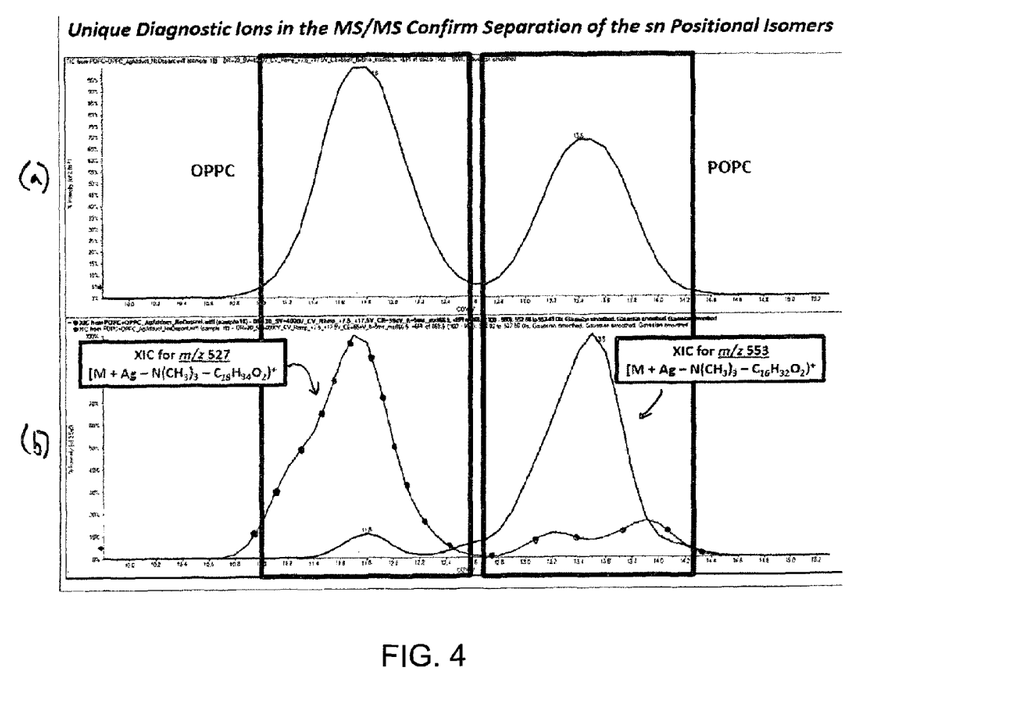
FIGS. 4A and 4B depicts data for a mixture of [POPC+Ag]+ and [OPPC+Ag]+ adducts as transmitted by a differential mobility spectrometer, subsequently fragmented, and detected in accordance with aspects of various embodiments of the applicant's teachings.

With reference now to FIGS. 3 and 4, exemplary plots depict the differential mobility separation of the two PC regioisomer standards (POPC and OPPC) after adducting the standards with a silver cation so as to form a PC isomer-metal ion adduct. Because the POPC and OPPC ion adducts are isomers, their ionization efficiency (response factor) should be equivalent such that their relative quantitation can be calculated based, for example, on the detected peak intensities of the ions transmitted by the differential mobility spectrometer. The data indicates that OPPC standard has a CV of ~11.8 V at peak intensity, whereas the CV is ~13.5 V at peak intensity for the POPC standard (a secondary peak is present at CV=~11.8 V). When the POPC and OPPC solutions are combined, the peaks remain resolved (unlike in FIG. 2 without adduction with a metal cation prior to DMS).

With specific reference to FIG. 4(b), the ion chromatograms for m/z 527 and 553 confirm that the resolved peaks of FIG. 3's mixture (the ionogram of the mixture in FIG. 3 is reproduced in FIG. 4(a)) correspond to the separated PC isomers. That is, FIG. 4B depicts the monitoring of an m/z unique to a particular fragment ion of each isomer lipid adduct following downstream MS/MS analysis.

These data also demonstrate that the tested Avanti's POPC standard contains an appreciable amount (~19%) of the OPPC regioisomer as a contaminant; this estimated contamination level is similar to that reported by Ekroos et al. (2003) using a method wherein MS/MS fragment ions were used to determine the contamination level. In scenarios where the relative abundances of these two lipids is differentiated by MS/MS fragment intensity ratios alone, such contamination of a purported "standard" could lead to loss of precision in the experiment. However, the DMS-based methods in accordance with various aspects of the applicants' teachings can provide the separation of the two regioisomeric lipid ion adducts prior to any downstream MS/MS experiments and help alleviate this potential issue.

Figure 5:
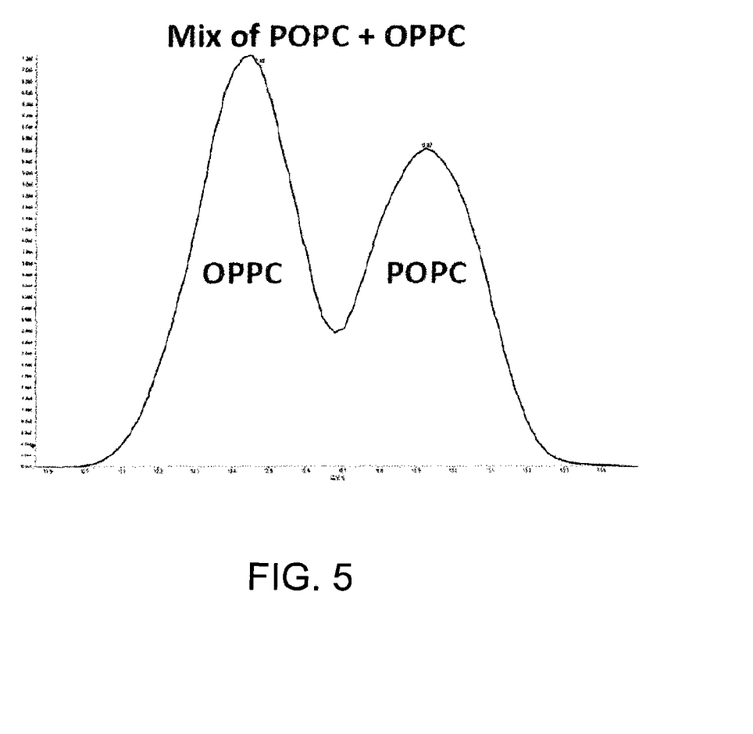
FIG. 5 depicts data for a mixture of [POPC+Li]$^+$ and [OPPC+Li]$^+$ adducts as transmitted by a differential mobility spectrometer and subsequently detected in accordance with aspects of various embodiments of the applicant's teachings.

With reference now to FIG. 5, the plot depicts the differential mobility separation of the two PC regioisomer standards (POPC and OPPC) after adducting the standards with a lithium cation so as to form a PC isomer-metal ion adduct. Inspection of FIG. 5 relative to FIG. 2 indicates that adduction of the lipid isomers with lithium prior to being transmitted through the DMS can also enable the separation of the POPC-lithium adduct and OPPC-lithium ion adduct to enable the relative quantitation of POPC and OPPC in the sample.

Without being bound to any particular theory, it is believed that the use of silver or lithium in the successful separation of these two lipid isomer metal ion adducts described above might arise from the ability of these metal ions to bond not only to lone pairs of electrons present on heteroatoms (like O and N), but also to pi electrons present in carbon-carbon multiple bonds (e.g., the alkene group present in the acyl chains of both OPPC and POPC). That is, the presence of an unsaturated carbon atom in the acyl chain of lipid isomers may enable the isomers to adduct with the cationization agent in such a manner so as to present to the DMS a sufficiently different structure that enables their separation.

Figure 6:
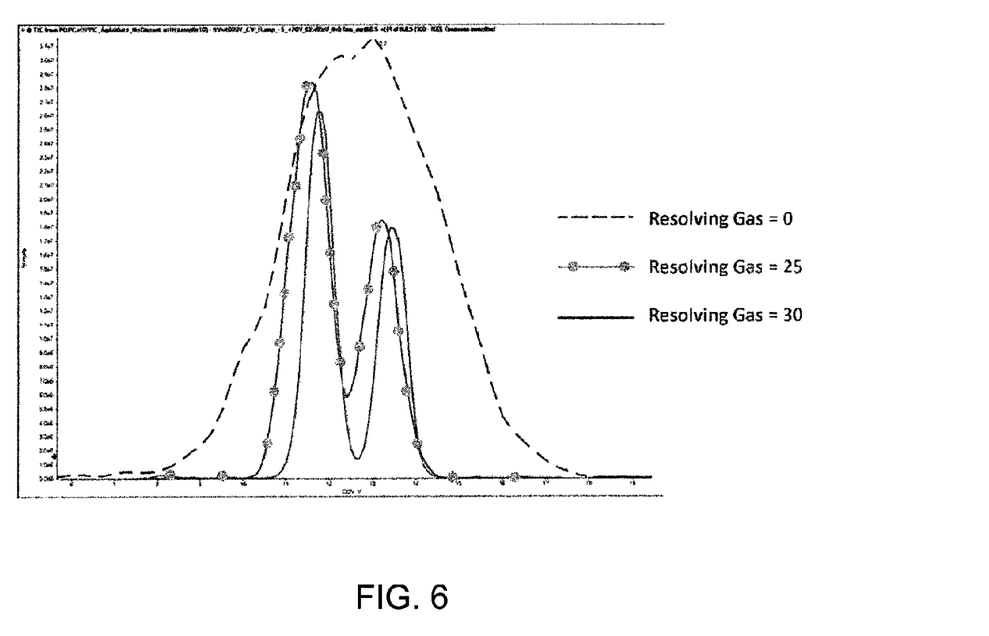
FIG. 6 depicts data for a mixture containing [POPC+Ag]$^+$ and [OPPC+Ag]$^+$ adducts as transmitted by a differential mobility spectrometer under various conditions of throttle gas and subsequently detected in accordance with aspects of various embodiments of the applicant's teachings.
Figure 7:
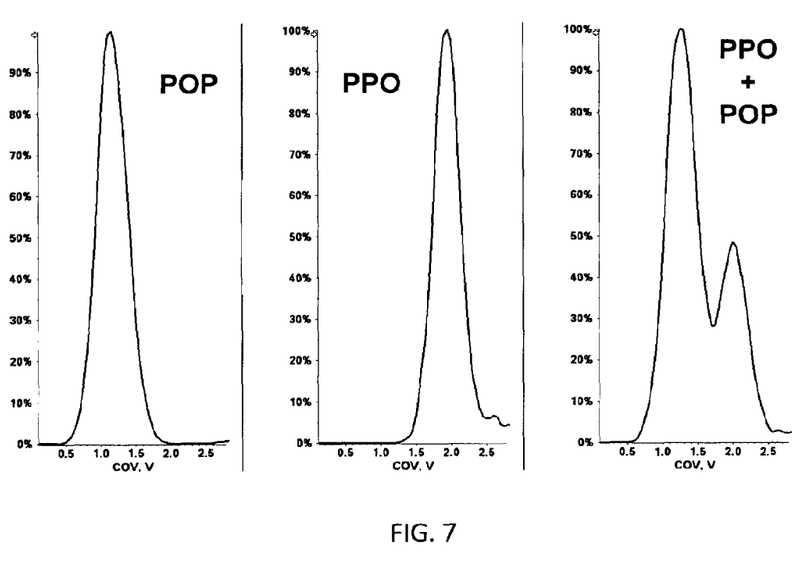
FIG. 7 depicts data from a POP+Ag adduct ion, PPO+Ag adduct ion, and a mixture thereof as transmitted by a differential mobility spectrometer operating with a chemical modifier and subsequently detected in accordance with aspects of various embodiments of the applicant's teachings.

As discussed above, differential mobility spectrometers for use in accord with teachings herein can have a variety of configurations, but are generally configured to resolve ions based on their mobility through a fixed or variable electric field. As will be appreciated by a person skilled in the art in light of the teachings herein, the various parameters used in the DMS can be altered, for example, in light of the isomers to be analyzed. With reference now to FIG. 6, for example, applicants have discovered that standard residence time for the POPC- and OPPC metal ion adducts within the DMS cell was not sufficient to afford separation of the ions in CV space. By adding gas at the outlet of the DMS electrodes (i.e., throttle gas), for example, residence time was increased so as to enable the separation of the isomer lipids metal ion adducts. That is, as indicated in FIG. 6, there was no separation between the species without throttle gas flowing (i.e., "Resolving Gas=0"). However, when the throttle gas flow was increased to 25 psi and 30 psi, clear separation of the two regioisomeric lipid metal ion adducts was obtained. The need for additional residence time for these two ions in order for separation to occur speaks to the potential subtle differences between the structures of these two regioisomeric ions.

Separation of TAG Isomers using Differential Mobility Spectrometry (DMS)

By combining metal cationization of the TAGs and the use of chemical modifiers in the DMS cell, TAG isomers can be separated.

A mixture of two TAG isomers—POP and PPO (described above)—were analyzed using electrospray ionization mass spectrometry (ESI-MS). Under more conventional operating conditions (e.g., TAGs sprayed from 50/50 methanol/dichloromethane with 5 mM ammonium acetate added), the two TAG isomers both appeared as ions of m/z 850.5 (corresponding to the ammoniated POP and PPO lipids). In addition to this convolution in m/z space, no separation was afforded using DMS; with the SV=4000V, only one peak was observed in the ionogram (plot of signal intensity versus ramped compensation voltage—CV).

When silver acetate (0.050 mM) was added to the TAG mixture solution, the ESI-MS analysis provided ions of m/z 939.5 (monoisotopic). When the DMS was engaged (SV=4000V, propanol chemical modifier, nitrogen throttle gas flowing), two distinct peaks in the DMS ionogram were observed as is depicted in the right ionogram of FIG. 7. Subsequent MS/MS spectra obtained at each of the two CVs revealed the presence of individual isomers at each CV—PPO and POP. The fragmentation was verified based upon examples in the literature of MS/MS of pure TAG lipids cationized by lithium. For comparison purposes, ionograms of a POP+silver only adduct ion and a PPO+silver only adduct ion are depicted in the left and center ionograms in FIG. 7, respectively.

Surprisingly, these data demonstrate that the use of a cationization agent with lipid regioisomers enables their separation using differential mobility spectrometry to allow for their specific and relative quantification in accordance with the teachings herein.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method for analyzing a sample, comprising:
   a. ionizing a sample containing or suspected of containing a plurality of lipid isomers so as to form one or more lipid silver adducts, at least one of the plurality of lipid isomers being selected from the group consisting of fatty acids, glycerolipids, glycerophospholipids, sphingolipids, saccharolipids, polyketides, sterol lipids, and prenol lipids, and wherein an acyl chain of the at least one of the plurality of lipid isomers comprises at least one unsaturated carbon-carbon double bond; and
   b. transporting said one or more lipid silver adducts through a differential mobility spectrometer to effect separation of said one or more lipid silver adducts;
   wherein ionizing the sample comprises reacting the sample with a salt of silver.

2. The method of claim 1, wherein the plurality of lipid isomers comprises 1 oleoyl-2-palmatoyl-sn-phosphatidylcholine and 1-palmatoyl-2-oleoyl-sn-phosphatidylcholine.

3. The method of claim 1, further comprising determining a relative abundance of the plurality of lipid isomers in the sample.

4. The method of claim 1, further comprising increasing a throttle gas flow rate to increase a drift time or a residence time of the lipid silver adducts in the differential mobility spectrometer.

5. The method of claim 1, wherein the sample is not passed through a liquid chromatography column prior to being transmitted through the differential mobility spectrometer.

6. The method of claim 1, wherein the differential mobility spectrometer comprises a high-field asymmetric waveform ion mobility spectrometry device.

7. The method of claim 1, further comprising:
   c. enhancing the separation of the lipid silver adducts by the addition of a chemical modifier to the differential mobility spectrometer.

8. The method of claim 7, wherein the chemical modifier used in the differential mobility spectrometer is selected from the group consisting of alcohols, aldehydes, amides, amines, aromatics, esters, ethers, halocarbons, ketones, nitriles, thiols, or water.

9. The method of claim 7, wherein the plurality of lipid isomers comprises isomeric triacylglycerol molecules.

10. The method of claim 9 wherein the isomeric triacylglycerol molecules comprise two palmetic acid groups and one oleic acid group.

11. The method of claim 9 wherein the chemical modifier is propanol.

12. A method of mass spectrometry, comprising:
   a. exposing a sample comprising a plurality of isomeric lipids to a cationization reagent so as to stabilize a configuration of said plurality of isomeric lipids, at least one of the plurality of isomeric lipids being selected from the group consisting of fatty acids, glycerolipids, glycerophospholipids, sphingolipids, saccharolipids, polyketides, sterol lipids, and prenol lipids, and wherein an acyl chain of the at least one of the plurality of isomeric lipids comprises at least one unsaturated carbon-carbon double bond and wherein said cationization reagent comprises a silver salt;
   b. transporting said stabilized isomeric lipids through an ion mobility spectrometer so as to effect separation of said plurality of one or more stabilized isomeric lipids;
   c. transporting the separated plurality of one or more stabilized isomeric lipids to a mass spectrometer for analysis.

13. A method for analyzing a sample containing or suspected of containing a plurality of isomeric lipids, at least one of the plurality of isomeric lipids being selected from the group consisting of fatty acids, glycerolipids, glycerophospholipids, sphingolipids, saccharolipids, polyketides, sterol lipids, and prenol lipids, and wherein an acyl chain of the at least one of the plurality of isomeric lipids comprises at least one unsaturated carbon-carbon double bond, the method comprising:
   a. forming one or more silver adducts with said isomeric lipids; and
   b. transporting said one or more silver adducts through a differential mobility spectrometer to effect separation of said one or more silver adducts.

* * * * *